(12) United States Patent
Pham et al.

(10) Patent No.: US 11,241,715 B2
(45) Date of Patent: Feb. 8, 2022

(54) ULTRASOUND SYSTEM AND ULTRASONIC PULSE TRANSMISSION METHOD

(71) Applicant: KONINKLIJKE PHILIPS N.V., Eindhoven (NL)

(72) Inventors: Hoa Pham, Eindhoven (NL); Ruediger Mauczok, Eindhoven (NL); Nico Maris Adriaan De Wild, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 174 days.

(21) Appl. No.: 15/738,159

(22) PCT Filed: Jun. 30, 2016

(86) PCT No.: PCT/EP2016/065440
§ 371 (c)(1),
(2) Date: Dec. 20, 2017

(87) PCT Pub. No.: WO2017/001636
PCT Pub. Date: Jan. 5, 2017

(65) Prior Publication Data
US 2018/0178250 A1    Jun. 28, 2018

(30) Foreign Application Priority Data
Jun. 30, 2015 (EP) .................................. 15174414

(51) Int. Cl.
*A61B 8/00* (2006.01)
*B06B 1/02* (2006.01)
(Continued)

(52) U.S. Cl.
CPC ............. *B06B 1/0215* (2013.01); *A61B 8/06* (2013.01); *A61B 8/4494* (2013.01); *A61B 8/483* (2013.01);
(Continued)

(58) Field of Classification Search
CPC .................................................. A61B 8/4494
See application file for complete search history.

(56) References Cited

U.S. PATENT DOCUMENTS

| 5,997,479 A | 12/1999 | Savord |
| 6,013,032 A | 1/2000 | Savord |

(Continued)

FOREIGN PATENT DOCUMENTS

| CN | 103976743 A | 8/2014 |
| JP | 2008510324 A | 4/2008 |

(Continued)

OTHER PUBLICATIONS

Oralkan et al. "Experimental Characterization of Collapse-Mode CMUT Operation", Aug. 2006, IEE Transactions on Ultrasonics, Ferroelectrics, and Frequency Control, vol. 53, No. 8, p. 1513-1523. (Year: 2006).*

(Continued)

*Primary Examiner* — Jason M Ip

(57) ABSTRACT

An ultrasound system comprises a probe including an array of CMUT (capacitive micromachined ultrasound transducer) cells. Each cell comprises a substrate carrying a first electrode. The substrate is spatially separated from a flexible membrane including a second electrode. The flexible membrane comprises a mass element in a central region. The system also comprises a voltage supply adapted to, in a transmission mode provide, the respective electrodes with a bias voltage driving the CMUT cells into a collapsed state and a stimulus voltage having a set frequency for resonating the flexible membrane of the CMUT cells in said collapsed state The mass element of the CMUT cells forces the central region of the flexible membrane to remain in the collapsed state during said resonating. A pulse transmission method for such a system is also disclosed.

16 Claims, 9 Drawing Sheets

(51) Int. Cl.
   *A61B 8/06* (2006.01)
   *A61B 8/08* (2006.01)
   *A61N 7/00* (2006.01)

(52) U.S. Cl.
   CPC ............... *A61B 8/488* (2013.01); *A61N 7/00* (2013.01); *B06B 1/0292* (2013.01); *B06B 2201/76* (2013.01)

(56) References Cited

U.S. PATENT DOCUMENTS

| | | | |
|---|---|---|---|
| 6,283,919 B1 | 9/2001 | Roundhill | |
| 6,328,697 B1 | 12/2001 | Fraser | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 8,327,521 B2 | 12/2012 | Dirksen et al. | |
| 8,397,574 B2 | 3/2013 | Tanaka et al. | |
| 9,539,854 B2 | 1/2017 | Klootwijk et al. | |
| 9,762,148 B2 | 9/2017 | Robinson et al. | |
| 10,092,270 B2 | 10/2018 | Dirksen | |
| 2004/0085858 A1* | 5/2004 | Khuri-Yakub | B06B 1/0688 367/181 |
| 2007/0215964 A1* | 9/2007 | Khuri-Yakub | B06B 1/0292 257/414 |
| 2010/0107485 A1 | 8/2010 | Dirksen | |
| 2010/0202254 A1* | 8/2010 | Roest | B06B 1/0292 367/180 |
| 2010/0207484 A1* | 8/2010 | Chang | B06B 1/0292 310/300 |
| 2010/0207485 A1* | 8/2010 | Dirksen | A61B 8/00 310/300 |
| 2011/0123043 A1* | 5/2011 | Felberer | H04R 19/005 381/94.2 |
| 2011/0163630 A1 | 7/2011 | Klootwijk et al. | |
| 2013/0128702 A1* | 5/2013 | Degertekin | G01S 15/89 367/140 |
| 2013/0331705 A1* | 12/2013 | Fraser | G01H 11/06 600/459 |
| 2014/0247698 A1* | 9/2014 | Dirksen | B06B 1/0292 367/189 |

FOREIGN PATENT DOCUMENTS

| | | |
|---|---|---|
| WO | 2005077012 A2 | 8/2005 |
| WO | 15/738159 A1 | 2/2012 |
| WO | 2014151525 A2 | 9/2014 |
| WO | 2015028314 A1 | 3/2015 |
| WO | 2015044827 A1 | 4/2015 |
| WO | 2015086413 A1 | 6/2015 |

OTHER PUBLICATIONS

Park et al "Comparison of Conventional and Collapse-Mode CMUT in 1-D Array Configuration" Ultrasonics Symposium, 2011, IEEE International p. 1000-1003.

Yongli Huang et al: "Capacitive micromachined ultrasonic transducers with piston-shaped membranes: fabrication and experimental characterization", IEEE Transactions on Ultrasonics, Ferr0electrics and Frequency Control,IEEE, US, vol. 56, No. 1,Jan. 31, 2009 (Jan. 31, 2009), pp. 136-145.

Rasim 0. Guldiken: "Dual-Electrode Capacitive Micromachined Ultrasonic Transducers for Medical Ultrasound Applications", Dec. 31, 2008 (Dec. 31, 2008),XP055232285, Retrieved from the Internet: URL:https://smartech.gatech.edu/bitstream/ handle/1853/31806/ guldiken_rasim_o_200812_ phd.pdf [retrieved on Nov. 30, 2015] paragraph [4.2.2].

Oralkan, Omer et al "Experimental Characterization of Collapse-Mode CMUT Operation", IEEE Transactions on Ultrasonics, Ferroelectrics, and Frequency Control, vol. 53, No. 8, Aug. 2006, pp. 1513-1523.

* cited by examiner (e)

(f)

(g)

ULTRASOUND SYSTEM AND ULTRASONIC PULSE TRANSMISSION METHOD

This application is the U.S. National Phase application under 35 U.S.C. § 371 of International Application No. PCT/EP2016/065440, filed on Jun. 30, 2016, which claims the benefit of EP Application Serial No. 15174414.1 filed Jun. 30, 2015. These applications are hereby incorporated by reference herein.

FIELD OF THE INVENTION

The present invention relates to an ultrasound system such as an ultrasound diagnostic imaging system or an ultrasound therapeutic system comprising a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap; and a voltage supply coupled to said electrode arrangement.

The present invention further relates to a method of ultrasonic pulse transmission using the probe of such an ultrasound system.

BACKGROUND OF THE INVENTION

Ultrasonic transducers used for medical imaging have numerous characteristics that lead to the production of high quality diagnostic images. Among these are broad bandwidth, affecting resolution and high sensitivity, which combined with pressure output affects depth of field of acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks. Firstly, the ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements. Moreover, PZT materials have poorly matched impedance to water or biological tissue, such that matching layers need to be added to the PZT materials in order to obtain the desired acoustic impedance matching with the medium of interest.

As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems.

The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the capacitive MUT (CMUT). CMUT transducers are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices generally can have dimensions in the 10-500 micrometer range, with the diaphragm diameter for instance being selected to match the diaphragm diameter to the desired resonance frequency (range) of the diaphragm, with spacing between the individual diaphragms less than a few micrometers. Many such individual CMUT cells can be connected together and operated in unison as a single transducer element. For example, four to sixteen CMUT cells can be coupled together to function in unison as a single transducer element. A typical 2D transducer array can have 2000-10000 CMUT transducer elements or cells by way of example.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for (multiple) matching layers and yields an improved effective bandwidth.

In order to optimize the acoustic power (output pressure) produced by the CMUT cells, the CMUT cells may be operated in so-called collapse mode in which the CMUT cells are driven by a bias voltage that drives a central part of the diaphragm or flexible membrane across the gap onto the opposing substrate and provided with a stimulus having a set frequency that causes the diaphragm or flexible membrane to resonate at the set frequency. This is for instance demonstrated by K. K. Park et al. in "Comparison of conventional and collapse-mode CMUT in 1-D array configuration", Ultrasonics Symposium (IUS), 2011 IEEE International, pages 1000-1003. However, a drawback of operating CMUT cells in a collapse mode is that it negatively affects the lifetime of the CMUT cells. The reasons for this are poorly understood.

SUMMARY OF THE INVENTION

The present invention seeks to provide an ultrasound system according to the opening paragraph having improved lifetime characteristics.

The present invention further seeks to provide a method of ultrasonic pulse transmission using the probe of such an ultrasound system.

According to an aspect, there is provided an ultrasound system comprising a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap, the flexible membrane comprising a mass element in a central region; and a voltage supply coupled to said probe and adapted to, in a transmission mode of the ultrasound system, provide the respective electrode arrangements of at least some of the CMUT cells with a voltage including a bias voltage component driving the at least some of the CMUT cells into a collapsed state in which a central part of the flexible membrane contacts the substrate, said central part including the central region; and a stimulus component having a set frequency for resonating the respective flexible membranes of the at least some of the CMUT cells in said collapsed state, wherein the mass element of each of the at least some CMUT cells forces at least the central region of the flexible membrane of said cell to remain in contact with the substrate during said resonating.

The present inventors have surprisingly found that the lifetime issues of CMUT cells operating in collapse mode during transmission is caused by the collapsed central part of the flexible membrane being temporarily released from the opposing substrate by the applied stimulus component. This increases the stress on the central part, which leads to cracking or other damage of the central part of the flexible membrane, thus compromising the lifetime of the CMUT cell. The present inventors have further found that this problem can be solved by placement of a mass element in the central portion of the flexible membrane, such that at least the central portion is forcibly retained in the collapsed state by the mass element during application of the stimulus. This reduces the stress induced in the central part of the flexible membrane and therefore increases its lifetime.

At this point it is noted that US 2007/0215964 A1 discloses a CMUT cell having a non-uniform membrane including a thickened portion in a central region of the membrane to alter the mass distribution of the CMUT cell. However, this non-uniformity is applied to increase the performance, i.e. output pressure, of the CMUT cell. There is no suggestion in this citation that such a thickened portion has any bearing on the lifetime of the CMUT cell, in particular on the lifetime of CMUT cells operated in a collapsed mode during transmission of ultrasonic pulses.

In an embodiment, each electrode arrangement further comprises a third electrode carried by the substrate, wherein the third electrode is located in between the first electrode and the second electrode and is electrically insulated from the first electrode by a dielectric layer, wherein the voltage supply is adapted to apply the stimulus across the respective first and second electrodes and to apply the bias voltage to the respective third electrodes of the at least some CMUT cells. This ensures that charge accumulation does not affect the output performance of the CMUT cells as this charge accumulation is not on the electrodes to which the stimulus is supplied.

The voltage supply may be further adapted to provide the respective electrode arrangements of at least some of the CMUT cells with a further voltage that forces the at least some CMUT cells in the collapsed state during a reception mode of said probe. This for instance may facilitate detection of a pulse echo at optimal sensitivity, i.e. by collapsing the CMUT cell to a degree where its corresponding resonance frequency matches the frequency of the expected echo signal.

The bias voltage supply advantageously comprises a first stage adapted to generate the bias voltage component of said voltage during said transmission mode, wherein the bias voltage component is sufficient to force the at least some CMUT cells in the collapsed state; and a second stage adapted to generate the stimulus component of said voltage. This has the advantage that the bulk of the voltage does not have to follow the relatively rapid modulation of the stimulus such that it can be produced using a voltage generator including large smoothing capacitors, thereby reducing the amount of noise in the overall voltage signal.

In an embodiment, the flexible membrane comprises a first material and the mass element comprises a second material, the second material having a higher density than the first material in order to maximize the mass in or on the central region of the flexible membrane. For example, the second material may be a metal or metal alloy, or a heavy non-metal material.

The mass element may be positioned on the flexible membrane, which is particularly advantageous for ease of manufacturing. Alternatively, the mass element may be integrated in the flexible membrane.

The mass element may have a cylindrical or annular shape, in particular if the flexible membrane is a circular membrane. In general, the shape of the mass element preferably matches the shape of the flexible membrane such that the mass is evenly distributed across the central region of the flexible membrane.

The ultrasound system may be an ultrasound diagnostic imaging system or an ultrasound therapeutic system.

According to another aspect, there is provided a method of ultrasonic pulse transmission, comprising providing a probe including an array of CMUT (capacitive micromachined ultrasound transducer) cells, each cell comprising a substrate carrying a first electrode of an electrode arrangement, the substrate being spatially separated from a flexible membrane including a second electrode of said electrode arrangement by a gap, the flexible membrane comprising a mass element in a central region; and providing the respective electrode arrangements of at least some of the CMUT cells with a voltage including a bias voltage component driving the at least some of the CMUT cells into a collapsed state in which a central part of the flexible membrane contacts the substrate, said central part including the central region; and a stimulus component having a set frequency for resonating the respective flexible membranes of the at least some CMUT cells in said collapsed state, wherein the mass element of each of at least some CMUT cells forces at least the central region of the flexible membrane of said cell to remain in contact with the substrate during said resonating.

By transmitting ultrasonic pulses in this manner, the flexible membrane of the CMUT cells of the probe are protected from damage caused by temporary release from the cell floor during pulse generation in a collapsed mode, thereby increasing the lifetime of the CMUT cells.

Each electrode arrangement may further comprise a third electrode carried by the substrate, wherein the third electrode is located in between the first electrode and the second electrode and is electrically insulated from the first electrode by a dielectric layer, the method further comprising applying the stimulus component across the respective first and second electrodes and applying the bias voltage component to the respective third electrodes of the at least some CMUT cells. This ensures that any charge accumulation does not affect the output performance of the CMUT cells as this charge accumulation is not on the electrodes to which the stimulus is supplied.

The method may further comprise periodically altering the set frequency to periodically alter a resonance frequency of the at least some CMUT cells such that transmit pulses of different frequency may be generated.

The method may further comprise periodically altering the bias voltage component driving the at least some of the CMUT cells into a collapsed state to alter the respective areas of the central parts of the at least some CMUT cells. This for instance may be done in conjunction with periodically altering the set frequency to periodically alter a resonance frequency of the at least some CMUT cells such that transmit pulses of different frequency may be generated such that each transmit pulse may be generated at maximized output pressure, as the output pressure of a CMUT cell transmitting at a given frequency is a function of the collapse area of its flexible membrane.

In an embodiment, the method further comprises providing, in a reception mode, the respective electrode arrangements of at least some of the CMUT cells with a further voltage forcing the at least some CMUT cells in the collapsed state in order to optimize the sensitivity of the receiving CMUT cells to a pulse echo of a particular frequency.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
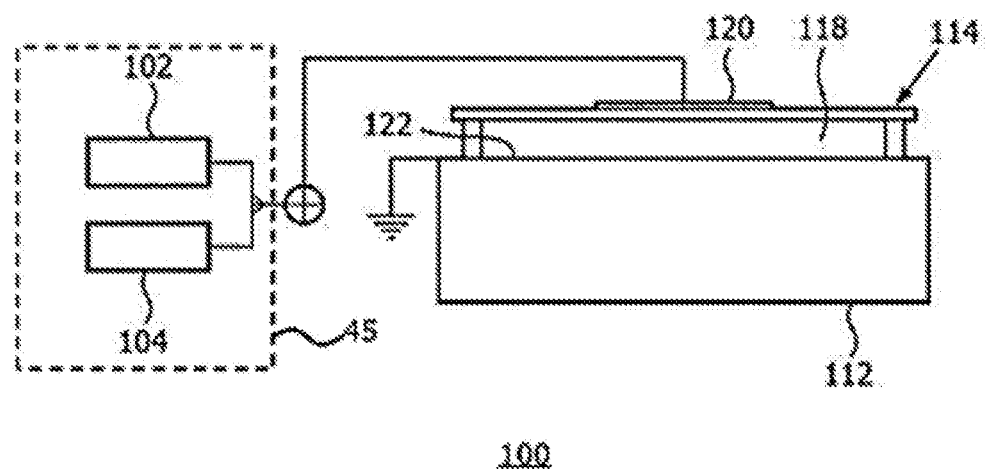
FIG. 1 schematically depicts a CMUT cell of an ultrasound system according to an embodiment operable in a collapsed mode.

It should be understood that the Figures are merely schematic and are not drawn to scale. It should also be understood that the same reference numerals are used throughout the Figures to indicate the same or similar parts.

FIG. 1 shows an aspect of an ultrasound system according to embodiments of the present invention, in which the system includes an ultrasound probe having a transducer array comprising CMUT cells 100. The CMUT cells 100 according to embodiments of the invention will be explained in more detail with the aid of FIG. 6-9. As will be explained in further detail below, such an ultrasound system may be an ultrasound diagnostic imaging system or may be an ultrasound therapeutic system. Such CMUT cell 100 typically comprises a flexible membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 122 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 1 the bottom electrode 122 is grounded by way of non-limiting example. Other arrangements, e.g. a grounded top electrode 120 or both top electrode 120 and bottom electrode 122 floating are of course equally feasible. The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

The bottom electrode 122 may be insulated on its cavity-facing surface with an additional layer (not pictured). A preferred electrically insulating layer is an oxide-nitride-oxide (ONO) dielectric layer formed above the substrate electrode 122 and below the membrane electrode 120 although it should be understood any electrically insulating material may be contemplated for this layer. The ONO-dielectric layer advantageously reduces charge accumulation on the electrodes which leads to device instability and drift and reduction in acoustic output pressure.

An example fabrication of ONO-dielectric layers on a CMUT is discussed in detail in European patent application EP 2,326,432 A2 by Klootwijk et al., filed Sep. 16, 2008 and entitled "Capacitive micromachined ultrasound transducer." Use of the ONO-dielectric layer is desirable with pre-collapsed CMUTs, which are more susceptible to charge retention than CMUTs operated with suspended membranes. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process.

Suitable CMOS processes are LPCVD and PECVD, the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser).

In FIG. 1, the diameter of the cylindrical cavity 118 is larger than the diameter of the circularly configured electrode plate 122. Electrode 120 may have the same outer diameter as the circularly configured electrode plate 122, although such conformance is not required. Thus, the membrane electrode 120 may be fixed relative to the top face of the membrane layer 114 so as to align with the electrode plate 122 below. The electrodes of the CMUT cell 100 provide the capacitive plates of the device and the gap 118 is the dielectric between the plates of the capacitor. When the diaphragm vibrates, the changing dimension of the dielectric gap between the plates provides a changing capacitance which is sensed as the response of the CMUT cell 100 to a received acoustic echo.

The spacing between the electrodes is controlled by applying a static voltage, e.g. a DC bias voltage, to the electrodes with a voltage supply 45. The voltage supply 45 may optionally comprise separate stages 102, 104 for providing the DC and AC or stimulus components respectively of the drive voltage of the CMUT cells 100, e.g. in transmission mode. The first stage 102 may be adapted to generate the static (DC) voltage component and the second stage 104 may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage for forcing the CMUT cells 100 into their collapsed states. This has the advantage that the first stage 102 may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component. Other suitable embodiments of the voltage source supply 45 should be apparent, such as for instance an embodiment in which the voltage source supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the voltage source supply 45 may be implemented in any suitable manner.

As is known per se, by applying a static voltage above a certain threshold, the CMUT cell 100 is forced into a collapsed state in which the membrane 114 collapses onto the substrate 112. This threshold value may depend on the exact design of the CMUT cell 100 and is defined as the DC bias voltage at which the membrane 114 sticks to (contacts) the cell floor by VanderWaals force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 2a and FIG. 3a.

Figure 2A:
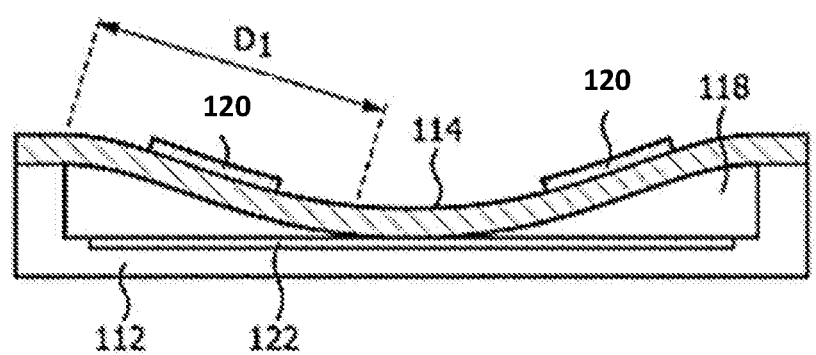
FIGS. 2A, 2B, 3A and 3B depict operating principles of such a CMUT cell.

The frequency response of a collapsed mode CMUT cell 100 may be varied by adjusting the DC bias voltage applied to the CMUT electrodes after collapse. As a result, the resonant frequency of the CMUT cell increases as a higher DC bias voltage is applied to the electrodes. The principles behind this phenomenon are illustrated in FIGS. 2a, 2b, 3a and 3b. The cross-sectional views of FIGS. 2a and 3a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 2a when a relatively low bias voltage is applied, whereas the distance D2 in FIG. 3a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 2a will be lower than the resonant frequency of the CMUT cell in FIG. 3a which is subject to the higher pulldown bias voltage.

Figure 2B:
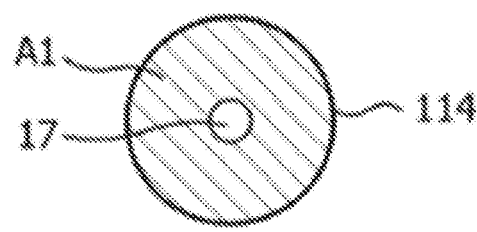
Figure 3A:
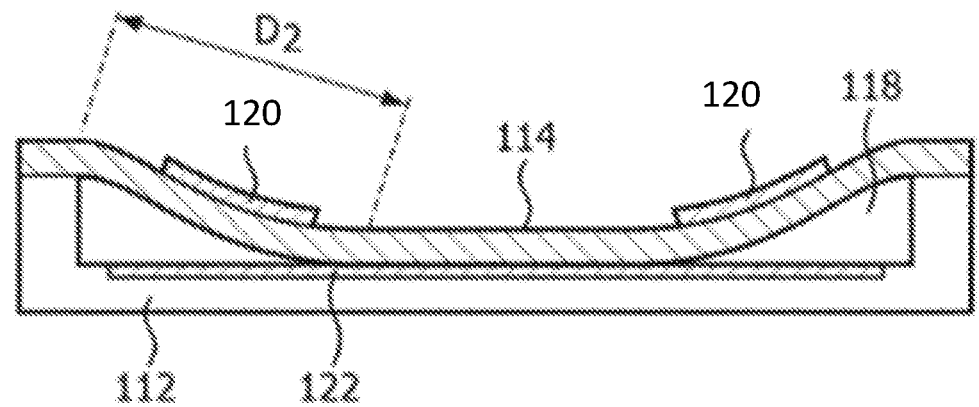
Figure 3B:
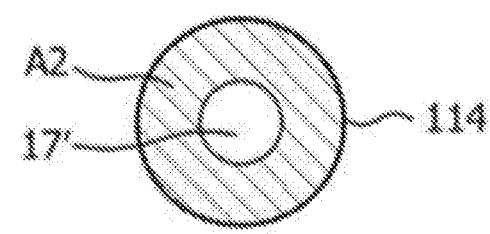

The phenomenon can also be appreciated from the two-dimensional illustrations of FIGS. 2b and 3b, as it is in actuality a function of the effective operating area of the CMUT membrane. When the membrane 114 just touches the floor of the CMUT cell as shown in FIG. 2a, the effective vibrating area A1 of the non-contacting (free vibrating) portion of the cell membrane 114 is large as shown in FIG. 2b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage as in FIG. 3a, the greater central contact area 17' results in a lesser free vibrating area A2 as shown in FIG. 3b. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4:
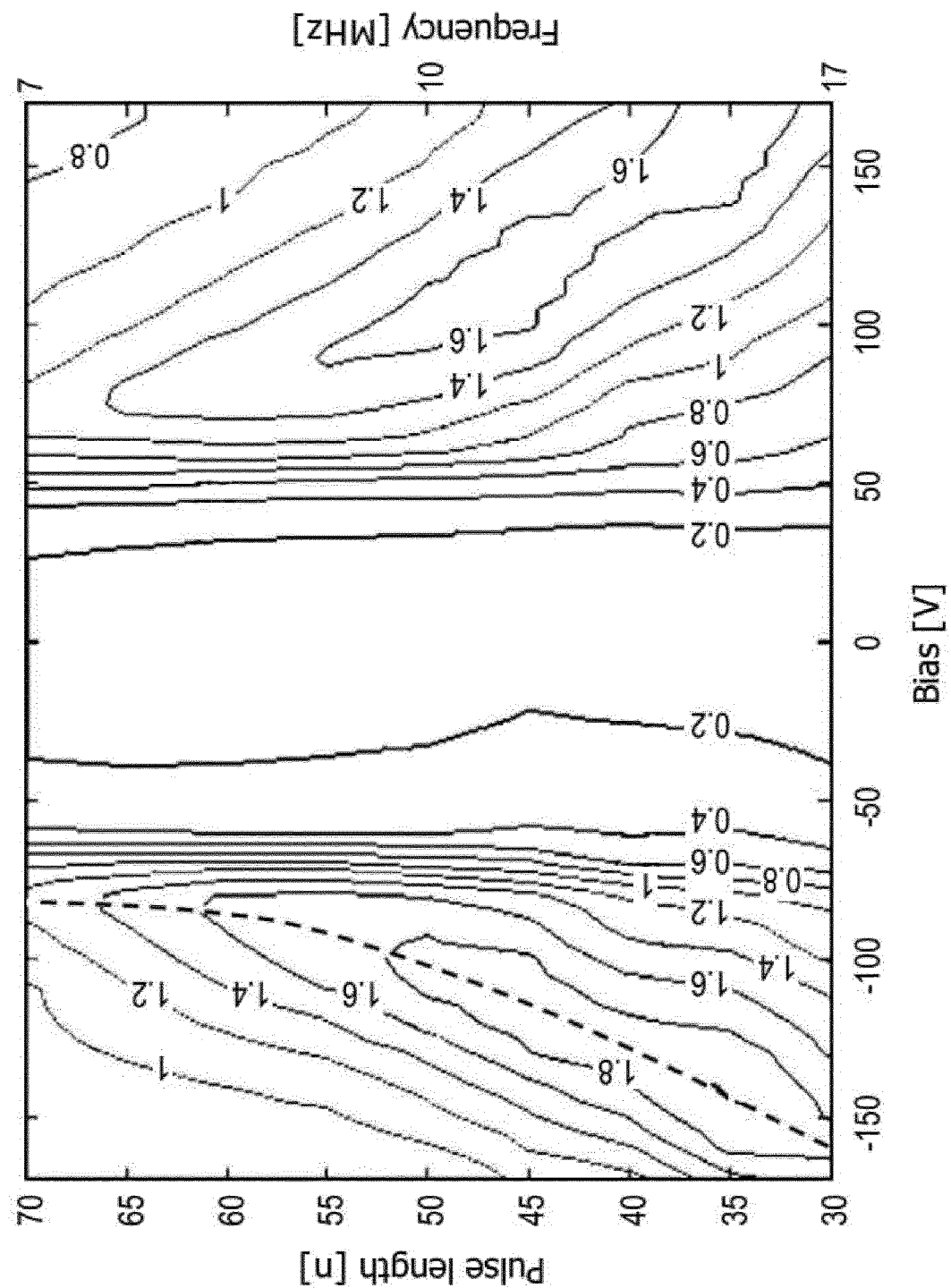
FIG. 4 is a contour plot of the acoustical performance of such a CMUT cell.

FIG. 4 shows a contour plot of the acoustical pressure output of a typical CMUT cell 100 in collapse mode as a function of applied DC bias voltage including a stimulus in the form of an AC modulation or frequency modulation of constant frequency during transmission. The corresponding pulse length is half the applied frequency. As can be seen from this contour plot, when the CMUT cell 100 is operated at a fixed or static voltage, e.g. a DC bias voltage of static value, optimal acoustic performance is obtained for a small range of frequencies only. However, when varying the bias voltage and the frequency modulation on the bias voltage signal in a correlated manner, as indicated by the dashed line in the contour plot, the optimal acoustic performance of the CMUT cell 100 may be achieved over a much larger frequency range, thereby increasing the effective bandwidth of the ultrasound pulse (or pulse train) generated in the transmission mode of the ultrasound probe including the CMUT cell 100.

This can be understood in back reference to FIGS. 2a and 3a, which explained that the resonance frequency of the CMUT cell 100 in a collapsed state is a function of the applied (DC) bias voltage. By adjusting the applied bias voltage when generating ultrasonic pulses of a particular set frequency by applying a stimulus having the appropriate set frequency, pulses of different frequencies can be generated exhibiting (near-)optimal acoustic performance of the CMUT cell 100 for each pulse frequency. This therefore ensures (near-) optimal imaging resolution over a large bandwidth of the imaging spectrum.

Figure 5:
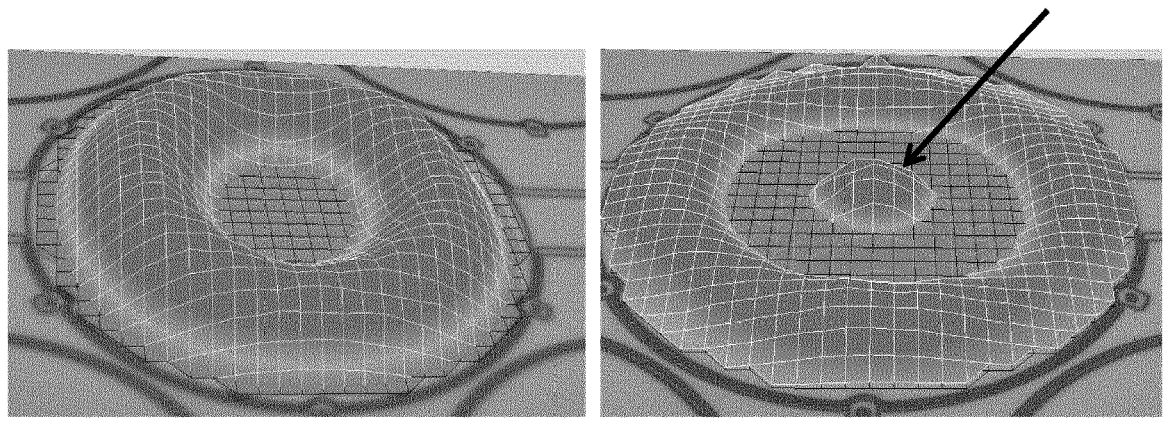
FIG. 5 depicts vibrometer images of the behaviour of a CMUT cell membrane in collapse mode when stimulated at different frequencies.

The inventors have found that an issue that occurs with transmitting pulses in this manner, i.e. with the flexible membrane 114 in a collapsed mode of the CMUT cell 100, is that the central part 17, 17' of the flexible membrane 114 in contact with the floor of the CMUT cell 100 is temporarily released from the floor during resonating the flexible membrane 114 in the collapsed mode as induced by the frequency modulated stimulus. This is shown in FIG. 5, which depicts a vibrometer image of a flexible membrane 114 in collapse mode stimulated with a low RF stimulus (left pane) and a high RF stimulus (right pane) respectively. The raised portions in these images indicate areas of the flexible membrane 114 in resonance. As can be seen, upon the applied stimulus reaching a critical frequency, the central region of the flexible membrane 114 starts to resonate as indicated by the arrow in the right hand pane of FIG. 5. This temporary release from the collapsed mode causes the central part 17, 17' of the flexible membrane 114 to experience increased stress levels, which over time damages, e.g. cracks, the central part 17, 17', leading to failure of the flexible membrane 114 and the CMUT cell 100 as a consequence.

Figure 6:
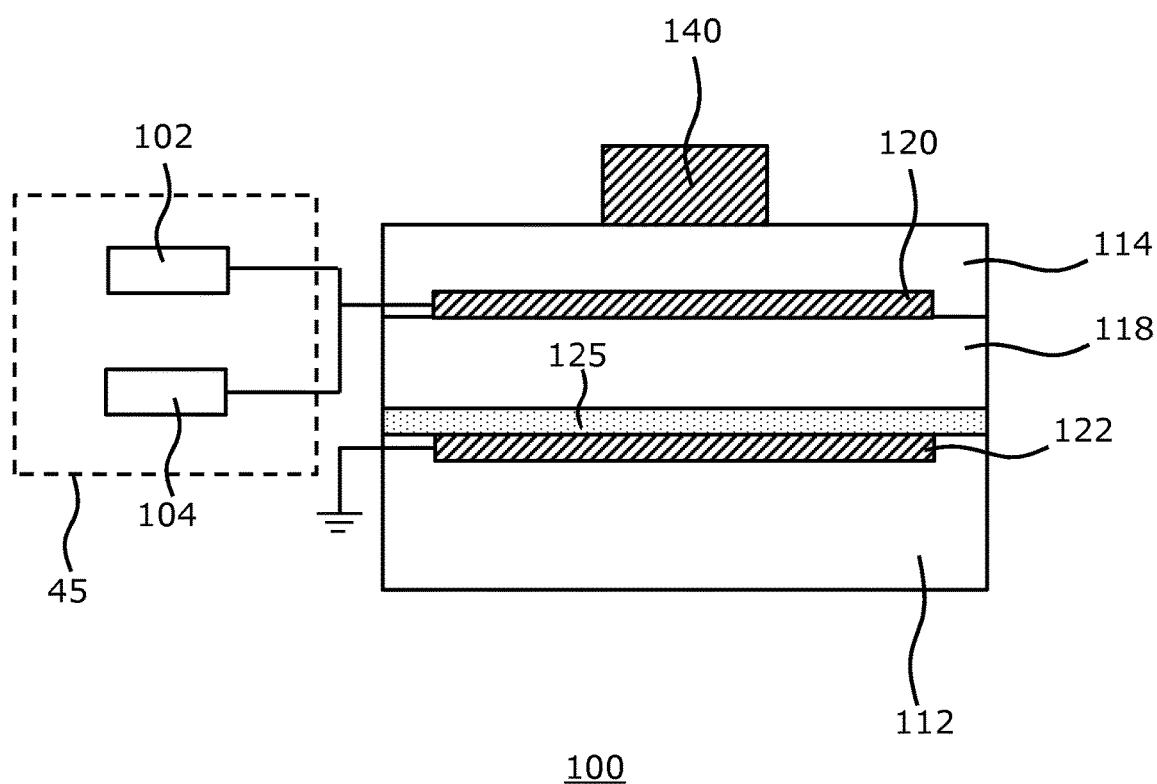
FIG. 6 schematically depicts a CMUT cell according to an embodiment.

The inventors have realized that such damage to the CMUT cell 100 may be prevented or at least delayed by including a mass element in or on the central region of the flexible membrane 114. An example embodiment of such a CMUT cell 100 is schematically depicted in FIG. 6. The CMUT cell 100 for instance may be as described in FIG. 1 with the inclusion of a mass element 140 on a central portion of the flexible membrane 114, which weighs down the central portion such that during transmission of ultrasound pulses with the CMUT cell 100 in a collapse mode as described above, the energy provided by the stimulus to the flexible membrane 114, in particular in the high energy or frequency part of the stimulus spectrum, is insufficient to temporarily release the central region of the flexible membrane 114 from the floor of the CMUT cell 100, thus preventing this central region from being exposed to the level of mechanical stress typically associated with this temporary release. Due to the fact that the mass element 140 is not permanently attached to the floor of the cavity 118, the flexible membrane 114 may be released from the cavity floor upon reduction or removal of the bias voltage. This furthermore allows the contact area of the flexible membrane 114 with the cavity floor to be tuned with the magnitude of the bias voltage as explained above. The reduced levels of stress to which the flexible membrane 114 is exposed during ultrasound pulse transmission in a collapsed mode by the presence of the mass element 140 thus improves the lifetime of the flexible membrane 114 and the CMUT cell 100.

The CMUT cell 100 comprises a bottom electrode 122 carried by the substrate 110 that may be insulated on its cavity-facing surface with an insulating layer 125 separating the bottom electrode 122 from the cavity 118. The bottom electrode 122 may be configured in any suitable manner, e.g. may be circularly configured and embedded into the cell floor of the CMUT cell 100. Insulating layer 125 preferably is a silicon dioxide ($SiO_2$) dielectric layer deposited in a TEOS-based deposition process such as a PECVD process. An alternative material for the insulating layer 123 may be oxide-nitride-oxide (ONO), high-k dielectrics and oxides (aluminium oxide, various grades including silane, $SiH_4$-based PECVD $SiO_2$, and so on).

The cavity 118 is covered by the flexible membrane 114 including an upper electrode 120, which may be exposed to the cavity 118 or separated from the cavity by an electrically insulating layer, e.g. part of the flexible membrane, e.g. to prevent a short circuit between exposed upper and lower electrodes 120, 122. The mass element 140 on the flexible membrane 114 preferably has an outline that matches the outline of the flexible membrane 114 such that the central region of the flexible membrane 114 is weighed down by the mass element 140 in a balanced manner. For example, for a circular flexible membrane 114, the mass element 140 preferably has a circular outline. Such a circular outline for instance may be achieved by the mass element 140 having an annular shape or a cylindrical shape, or any other 3-dimensional shape with a circular outline.

The mass element 140 preferably is a heavy mass element to ensure that the central region of the flexible membrane 114 remains collapsed when being stimulated by the stimulus provided by voltage source 45 in a transmit mode of the ultrasound system. This may be achieved by controlling the dimensions of the mass element 140, preferably the height of the mass element 140 as increasing the width or diameter of the mass element 140 may compromise the output characteristics of the CMUT cell 100. Preferably, the mass element 140 comprises or consists of a material having a high density, preferably a higher density than the material or materials of the flexible membrane 114, as this facilitates a minimization of the dimensions of the mass element 140 when designing a mass element 140 having the desired critical mass. Any suitable high-density material may be used for this purpose, e.g. heavy metals or metal alloys including one or more heavy metals. Particularly preferred are metals or metal alloys that are compatible with CMOS process technology, such as W, TiW, and so on, as this facilitates straightforward manufacture of the mass element 140 in a CMOS process requiring minimal adjustment of the CMOS process.

Figure 7:
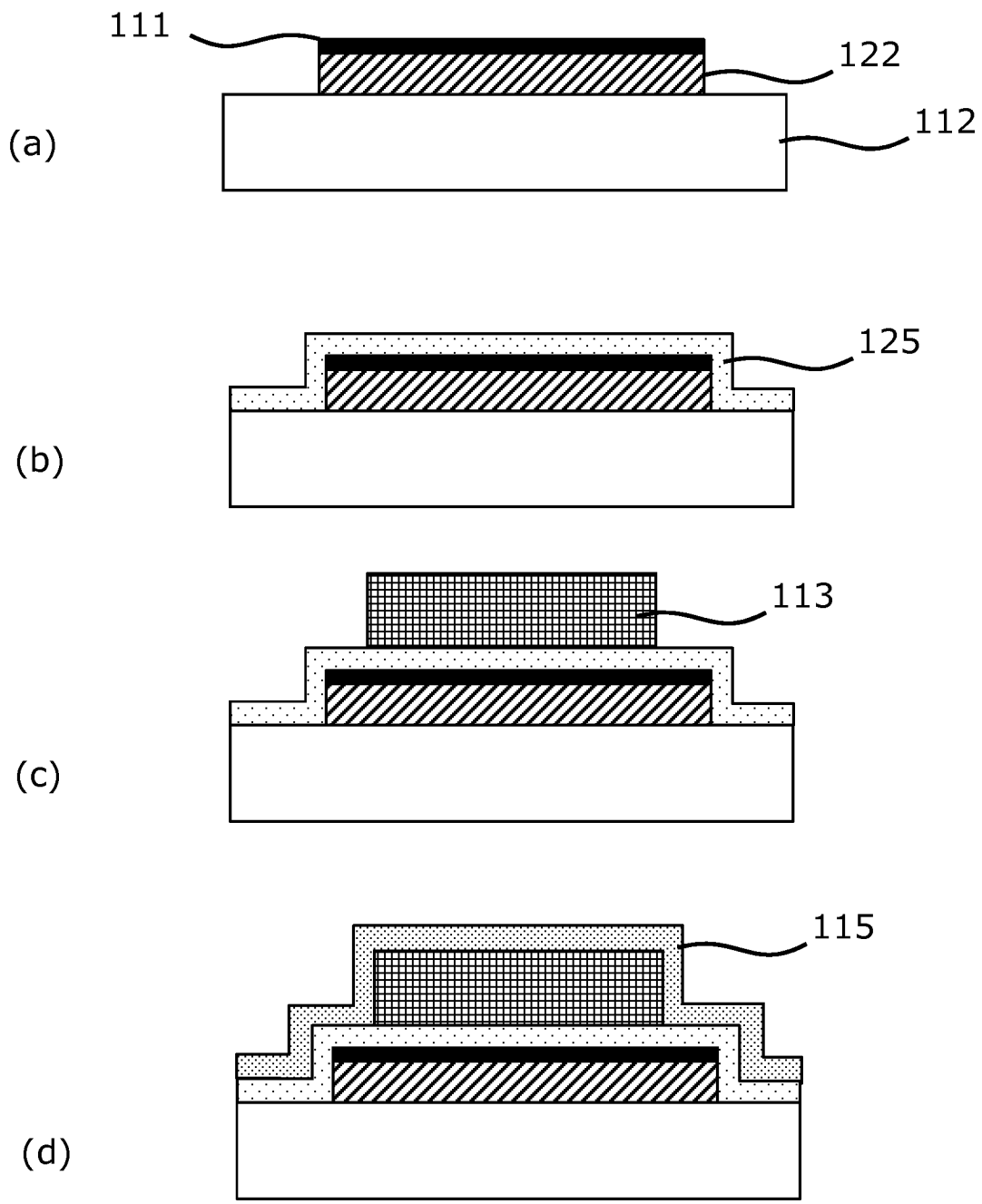
FIG. 7 schematically depicts an example manufacturing method of the CMUT cell of FIG. 6.
Figure 7:
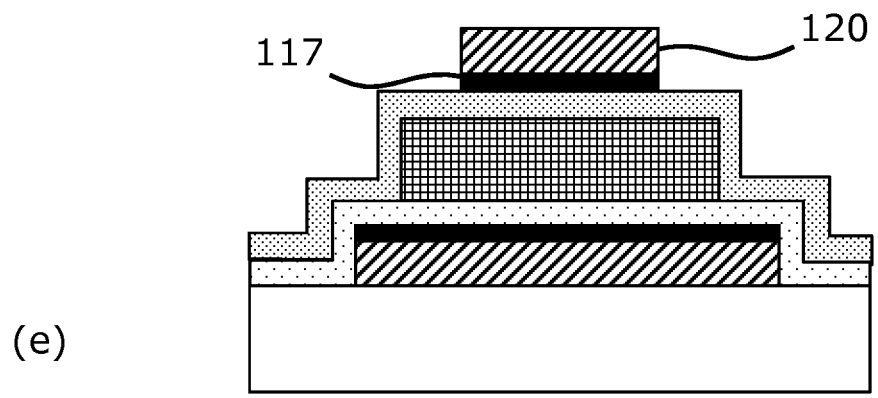
Figure 7:
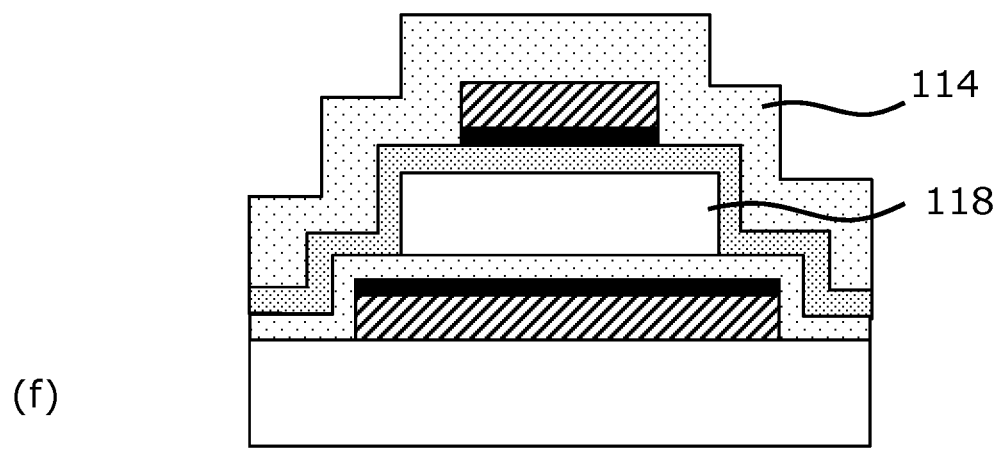
Figure 7:
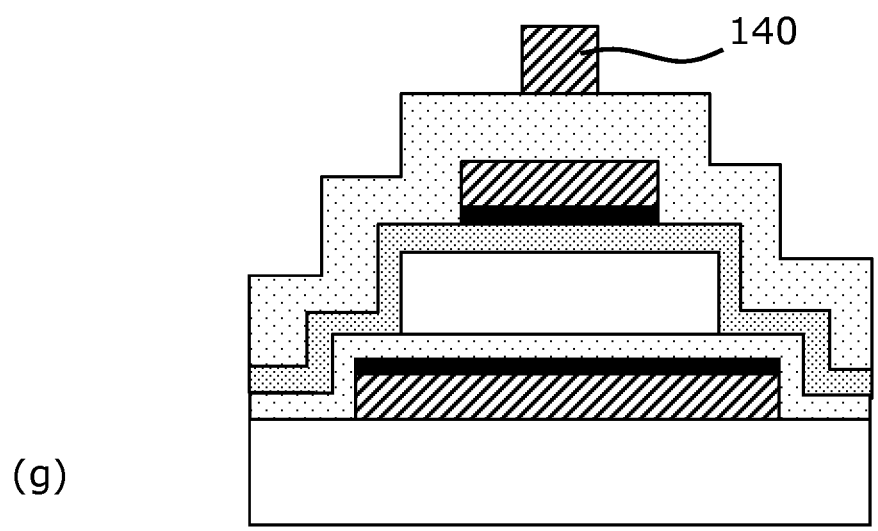

A non-limiting example of such a manufacturing process will be described in more detail with the aid of FIG. 7, which schematically depicts key CMOS processing steps for the inclusion of a mass element 140 on a flexible membrane 114 of a CMUT cell 100. In step (a), the bottom electrode layer with optional barrier layer is formed on a silicon wafer 112 in any suitable manner, e.g. through sputtering, after which the layers are etched, e.g. dry-etched, to form the bottom electrode 122 optionally covered by barrier layer 111. The silicon wafer 112 may be any suitable silicon wafer, such as for example a silicon wafer having a thermal silicon oxide top layer, an ASIC substrate, and so on. Suitable barrier layer materials may include but are not limited to high work function materials such as TiN, TiW and so on.

In optional step (b), a first dielectric layer 125 may be formed over the bottom electrode 122, e.g. through a deposition process such as PECVD. Suitable materials for the first dielectric layer 125 include but are not limited to $SiO_2$, preferably formed through a TEOS deposition process, oxide-nitride-oxide (ONO), high-k dielectrics and oxides such as aluminium oxide, various grades including silane, $SiH_4$-based PECVD $SiO_2$, and so on. $SiO_2$ formed through a PECVD deposition process of TEOS is particularly preferred.

Next, as depicted in step (c), a sacrificial material 113 is deposited over the resulting structure and subsequently patterned to define the outline of the cavity 118 to be formed, after which in an optional step (d) a further dielectric layer 115 may be formed over the resulting structure, e.g. through deposition such as PECVD. Suitable sacrificial materials 113 include but are not limited to metals, metal alloys, layer stacks including a metal layer with a capping layer, amorphous silicon and so on. Aluminium alloys such as Al/Nd and Al/Mo are particularly suitable. Suitable materials for the further dielectric layer 115 include but are not limited to $SiO_2$, preferably formed through a TEOS deposition process, oxide-nitride-oxide (ONO), high-k dielectrics and oxides such as aluminium oxide, various grades including silane, $SiH_4$-based PECVD $SiO_2$, and so on. $SiO_2$ formed through a PECVD deposition process of TEOS is particularly preferred.

In step (e), a further barrier layer and further electrode layer are formed or deposited in any suitable manner, e.g.

through sputtering, after which the layers are etched, e.g. dry-etched, to form the upper electrode 120 optionally separated from the underlying structure by further barrier layer 117. Next, the flexible membrane 114, e.g. a membrane formed of one or more high breakdown materials such as silicon nitride or any other suitable material, is formed over the upper electrode 120 and underlying structure, e.g. through any suitable deposition technique, after which a vent hole or chimney (not shown) is formed through the flexible membrane 114 through which the sacrificial material 113 is removed, thereby forming the cavity 118, after which the vent hole or chimney is sealed in any suitable manner, as is known per se. For example, the sealing process may be carried out under vacuum conditions using PECVD deposition or sputtering, in which a sealing material, e.g. SiN, TEOS, an oxide-nitride-oxide material stack, metal, and so on, is deposited in the vent hole to seal it. As will be readily understood by the skilled person, the pressure difference between the pressure inside the cavity 118 and the external pressure will determine the shape of the flexible membrane 114 in air.

Finally, the mass element 140 is formed on the flexible membrane 114 in a central region of the flexible membrane 114 as shown in step (g). The mass element 140 may formed by depositing a layer of the material(s) that form the mass element 140, e.g. TiW and/or W layer(s), and patterning this layer (or these layers), e.g. through etching, in order to form the mass element 140. The mass element 140 may be seen to form a pillar on the flexible membrane 114, e.g. an annular or cylindrical pillar in case of a circular flexible membrane 114, in order to weigh down the central portion of the flexible membrane 114 for the previously explained purpose of retaining this central portion on the floor of the CMUT cell 100 during the generation of transmit pulses with the cell in a collapsed mode.

This manufacturing process requires a single additional mask only, i.e. to pattern the mass element 140, and therefore requires minimal adjustment of a CMOS manufacturing process to include the mass element 140 in the CMUT cell 100. Nevertheless, it will be readily understood that many other suitable manufacturing routes to the inclusion of such a mass element 140 in the CMUT cell 100 are readily available, e.g. the routes disclosed in US 2007/0215964 A1, and that any suitable manufacturing process may be contemplated.

In an embodiment, the mass element 140 may be formed to include an intrinsic internal stress, e.g. by forming the mass element at elevated temperatures such that thermal stresses are induced in the mass element 140 by cooling, or in any other suitable manner, the relaxation of which stresses can be used to force the flexible membrane 114 in a predefined shape, e.g. a pre-collapsed shape in which the central region of the flexible membrane 114 is forced towards the floor of the CMUT cell 100.

Figure 8:
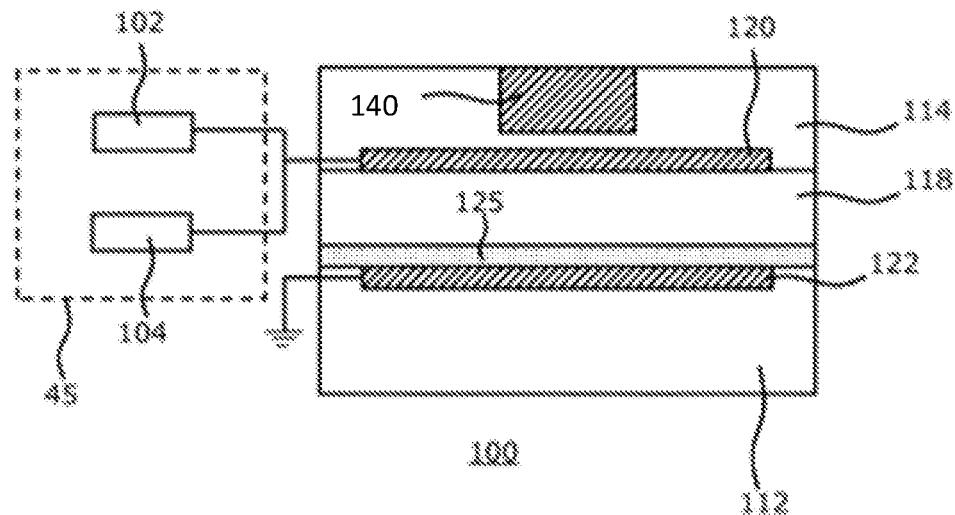
FIG. 8 schematically depicts a CMUT cell according to another embodiment.

FIG. 8 schematically depicts an alternative embodiment of a CMUT cell 100, in which the mass element 140 is integrated in the flexible membrane 114. This has the advantage that the overall height of the CMUT cell 100 is reduced. The mass element 140 may be integrated in the flexible membrane 114 in any suitable manner, for instance by depositing part of the flexible membrane 114 to a first thickness in step (f) of FIG. 7, subsequently forming the mass element 140 on the partially formed flexible membrane 114 as per step (g) in FIG. 7 and subsequently completing the formation of the flexible membrane 114 by forming, e.g. depositing, the remainder of the flexible membrane 114 over the resulting structure, optionally followed by a planarization step using upper surface of the mass element 140 as a stop for the planarization step.

Figure 9:
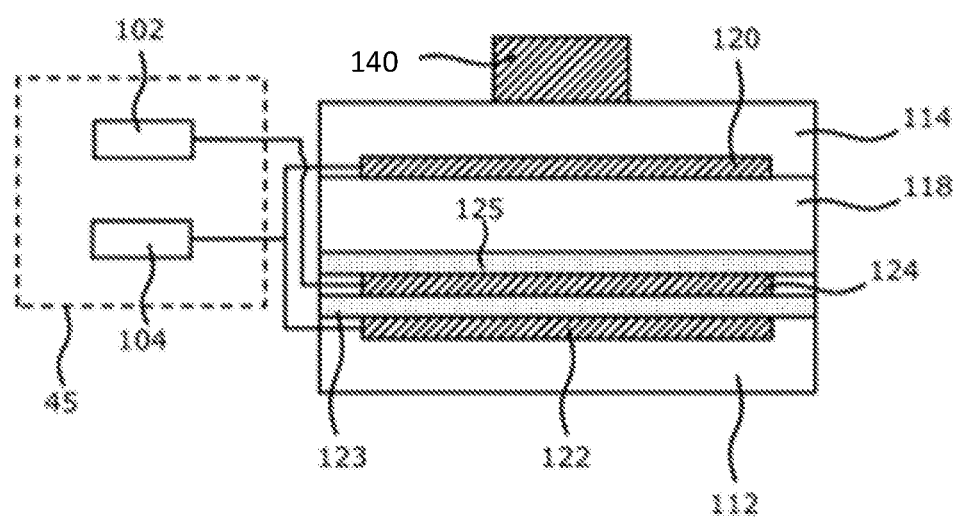
FIG. 9 schematically depicts a CMUT cell according to yet another embodiment.

FIG. 9 schematically depicts another embodiment of a CMUT cell 100 including a mass element 140 on the flexible membrane 114 as described above. In this embodiment, the CMUT cell 100 is a 3-electrode CMUT cell 100. This CMUT cell 100 includes a third electrode 124 embedded into the floor of the cell 100 comprising an upper surface of the substrate 112. The bottom electrode 122 may be configured in any suitable manner, e.g. may be circularly configured and embedded into the cell floor.

The third electrode 124 is typically insulated on its cavity-facing surface with an upper insulating layer 125 and insulated on its bottom electrode-facing surface with a bottom insulating layer 123. Insulating layers 123 and 125 preferably are silicon dioxide ($SiO_2$) dielectric layers deposited in a TEOS-based deposition process such as a PECVD process. An alternative material for the insulating layers 123, 125 may be oxide-nitride-oxide (ONO), high-k dielectrics and oxides (aluminium oxide, various grades including silane, $SiH_4$-based PECVD $SiO_2$, and so on).

In this embodiment, the first electrode 120 and third electrode 124 of the CMUT cell 100 provide the capacitive plates of the CMUT device, whereas the capacitive coupling between the third electrode 124 and the second electrode 122 through the bottom dielectric layer 123 defines a capacitor, e.g. for a RC filter, which may be integrated in the CMUT cell 100. The first electrode 120 may be brought in vibration by means of a voltage supply 45 adapted to apply an AC stimulus with a set frequency over the second electrode 122 and the first electrode 120, which results in the generation of an acoustic beam, e.g. an acoustic pulse of a particular frequency bandwidth, whereas the third electrode 124 is provided with the DC component of the drive voltage. This has the advantage that the stored charge related to the DC component may be isolated from a user or patient. As before, it will be understood that although the mass element 140 is shown on the flexible membrane 114 in this embodiment, it is equally feasible that the mass element 140 is integrated in the flexible membrane.

Figure 10:
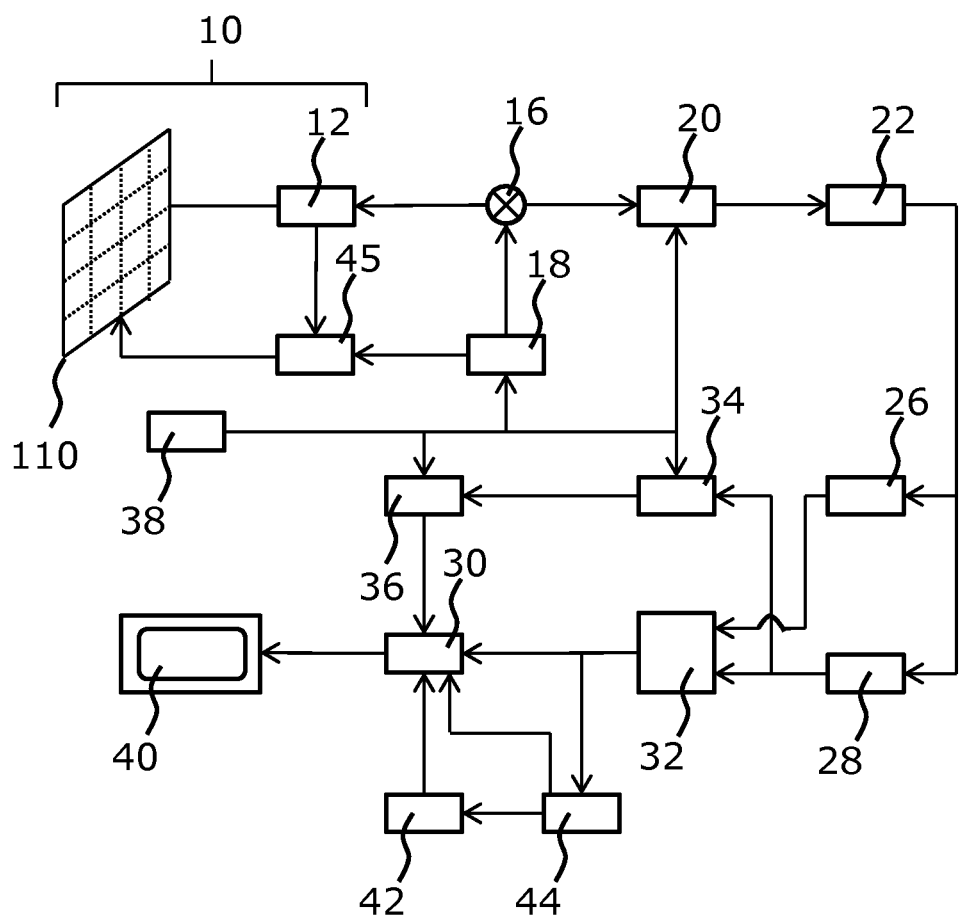
FIG. 10 schematically depicts an example embodiment of an ultrasound diagnostic imaging system.

In FIG. 10, an ultrasonic diagnostic imaging system with an array transducer probe according to an example embodiment of the present invention is shown in block diagram form. In FIG. 10 a CMUT transducer array 110 is provided in an ultrasound probe 10 for transmitting ultrasonic waves and receiving echo information. The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial wire, to a transmit/receive (T/R) switch 16 which switches between transmission and reception modes and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control the aforementioned voltage source 45 for the CMUT array. For instance, the voltage source 45 sets the DC and AC bias voltage(s) that are applied to the CMUT cells 100 of a CMUT array 110, e.g. to generate the chirped pulses in transmission mode as explained above.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 100. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

Moreover, it will be understood that the present invention is not limited to an ultrasonic diagnostic imaging system. The teachings of the present invention are equally applicable to ultrasonic therapeutic systems in which the CMUT cells 100 of the probe 10 may be operable in transmission mode only as there is no need to receive pulse echoes. As will be immediately apparent to the skilled person, in such therapeutic systems the system components described with the aid of FIG. 10 and required to receive, process and display pulse echoes may be omitted without departing from the teachings of the present application.

Figure 11:
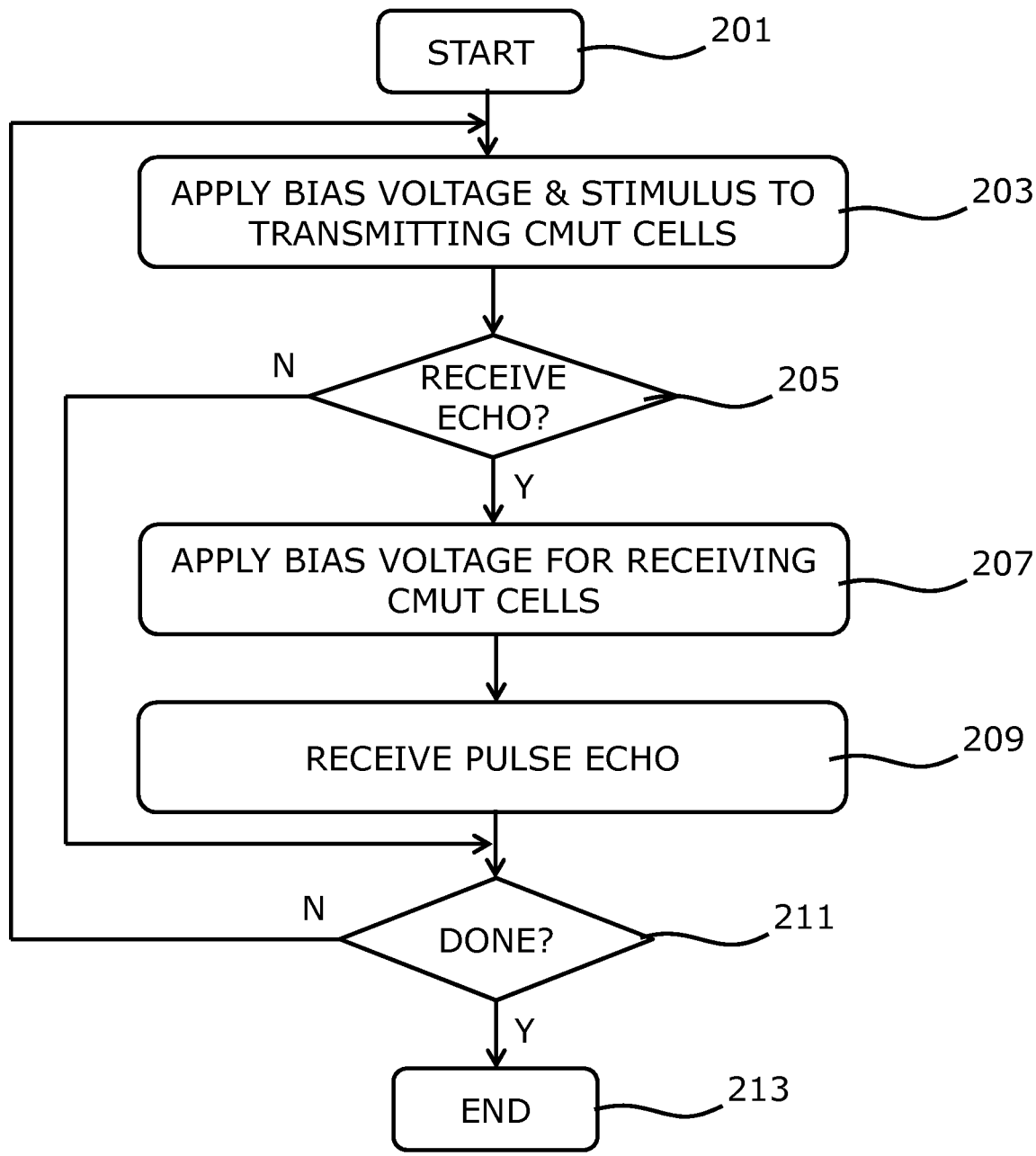
FIG. 11 depicts a flow chart of a pulse transmission method according to an embodiment.

FIG. 11 schematically depicts a flowchart of a method 200 of ultrasonic pulse transmission, for instance using an embodiment of an ultrasonic diagnostic imaging system or ultrasonic therapeutic system described above. The method 200 starts in step 201 with the provision of a probe 10 according to an embodiment of the present invention, i.e. a probe 10 including an array 110 of CMUT cells 100, each cell comprising a substrate 112 carrying a first electrode 122 of an electrode arrangement, the substrate being spatially separated from a flexible membrane 114 including a second electrode 120 of said electrode arrangement by a gap 118, the flexible membrane 114 comprising a mass element 140 in a central region 17, 17' of the flexible membrane 114.

In a transmission mode, the method 200 proceeds to step 203 in which the electrodes of the CMUT cells 100 selected for transmission are provided with a the respective electrode arrangements of the selected CMUT cells with a voltage including a bias voltage component driving the selected CMUT cells 100 into a collapsed state in which a central part 17, 17' of the flexible membrane 114 contacts the substrate 112 and a stimulus component having a set frequency for resonating the respective flexible membranes 114 of the selected CMUT cells 100 in the collapsed state, wherein the mass element 140 of each of the selected CMUT cells 100 forces the central region 17, 17' of the flexible membranes 114 the selected CMUT cells 100 to remain in contact with the substrate during said resonating. In an embodiment, the bias voltage component is set in accordance with the principles explained with the aid of FIG. 4, in which the area of collapse of the selected CMUT cells 100 is controlled by the application of an appropriate bias voltage such that the output pressure of the selected CMUT cells 100 for the pulses generated by the application of the stimulus to the selected CMUT cells 100 is maximized. Any suitable number of CMUT cells 100 may be selected in a single transmit cycle, e.g. all CMUT cells 100 in the array 110, a plurality of the CMUT cells 100, which plurality forms a subset of all CMUT cells 100 in the array 110, e.g. a cluster of CMUT cells 100 of the array 110, or a single CMUT cell 100.

Upon completion of the transmit cycle, it is decided in step 205 if the array 110 should be switched to a receive mode. This may not be the case if a further transmit cycle is to be performed as decided in step 211 and/or if the pulses are transmitted in the context of an ultrasound therapeutic system as explained above. If no receive mode should be invoked, it is checked in step 211 if another transmit cycle should be invoked. If this is the case, the method 200 returns to step 203 to apply a bias voltage and stimulus to a selection of CMUT cells 100 of the array 110, which selection may be the same selection or a different selection of CMUT cells 100.

The applied bias voltage may be the same bias voltage as applied in the previous transmission cycle or may be a different bias voltage, i.e. the bias voltage may be periodically altered, which each period corresponding to a single transmission cycle. Similarly, the stimulus may be the same stimulus as applied in the previous transmission cycle or a different stimulus, i.e. a stimulus of different set frequency, i.e. the stimulus may be periodically altered, which each period corresponding to a single transmission cycle. For example, a stimulus of different set frequency may be applied if the ultrasound system is to transmit a series of pulses of different frequencies into the issue of a patient. In an embodiment, the bias voltage component is set in accordance with the principles explained with the aid of FIG. 4, in which the area of collapse of the selected CMUT cells 100 is controlled by the application of an appropriate bias voltage such that the output pressure of the selected CMUT cells 100 for the pulses generated by the application of the stimulus to the selected CMUT cells 100 is maximized.

If on the other hand it is decided in step 205 that the ultrasound system is to be switched to a receive mode, the method proceeds to step 207 in which a selection of CMUT cells 100 of the array 110 are provided with a bias voltage, preferably a bias voltage to drive the selection of CMUT cells 100 into a collapsed state. Preferably, the area of collapse of the flexible membranes 114 of the selection of CMUT cells 100 is tuned by selecting the strength of the bias voltage such that the selection of CMUT cells 100 have optimal sensitivity to the frequency of the expected pulse echo, after which the pulse echo is received in step 209 and further processed in any suitable manner. Upon completion of the transmit and optional receive cycles, the method 200 terminates in step 213.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An ultrasound system comprising:
a probe including an array of CMUT (capacitive micromachined ultrasound transducer) cells, each cell configured to operate in a collapsed state and comprising:
a substrate;
a flexible membrane including a central region, wherein the substrate is spatially separated from the flexible membrane by a gap, wherein the central region is configured to contact the substrate in the collapsed state;

an electrode arrangement comprising a first electrode in contact with the substrate and a second electrode in contact with the flexible membrane; and a mass element disposed at the central region of the flexible membrane such that at least a portion of the flexible membrane is disposed between the second electrode and the mass element, wherein the mass element is different from the flexible membrane, the first electrode, and the second electrode, wherein the mass element is configured to force the central region to remain in contact with the substrate while the flexible membrane resonates at a frequency in the collapsed state such that the central region does not temporarily release from the substrate while the flexible membrane resonates at the frequency in the collapsed state; and a voltage supply coupled to said probe and adapted to, in a transmission mode of the ultrasound system, provide the respective electrode arrangement of at least some of the CMUT cells with a voltage including:
  a bias voltage component driving the at least some of the CMUT cells into the collapsed state; and
  a stimulus component for resonating the respective flexible membrane of the at least some of the CMUT cells at the frequency in said collapsed state, wherein the stimulus component comprises the frequency, wherein the mass element of each of the at least some CMUT cells permits release of said central region from the substrate upon reduction or removal of said bias voltage component.

2. The ultrasound system of claim 1, wherein each electrode arrangement further comprises a third electrode carried by the substrate, wherein the third electrode is located in between the first electrode and the second electrode and is electrically insulated from the first electrode by a dielectric layer, wherein the voltage supply is adapted to apply the stimulus component across the respective first and second electrodes and to apply the bias voltage component to the respective third electrode of the at least some CMUT cells.

3. The ultrasound system of claim 1, wherein the voltage supply is further adapted to provide the respective arrangement of at least some of the CMUT cells with a further voltage that forces the at least some CMUT cells in the collapsed state during a reception mode of said probe.

4. The ultrasound system of claim 1, wherein the voltage supply comprises:
  a first stage adapted to generate the bias voltage component of said voltage during said transmission mode, wherein the bias voltage component is sufficient to force the at least some CMUT cells in the collapsed state; and
  a second stage adapted to generate the stimulus component of said voltage.

5. The ultrasound system of claim 1, wherein the flexible membrane comprises a first material and the mass element comprises a second material, the second material having a higher density than the first material.

6. The ultrasound system of claim 5, wherein the second material is a metal or metal alloy, or a heavy non-metal material.

7. The ultrasound system of claim 1, wherein the mass element is positioned on the flexible membrane.

8. The ultrasound system of claim 1, wherein the mass element is integrated in the flexible membrane.

9. The ultrasound system of claim 1, wherein the mass element has a cylindrical or annular shape.

10. The ultrasound system of claim 1, wherein the ultrasound system is an ultrasound diagnostic imaging system or an ultrasound therapeutic system.

11. A method of ultrasonic pulse transmission, comprising:
  providing a probe including an array of CMUT (capacitive micromachined ultrasound transducer) cells, each cell configured to operate in a collapsed state and comprising:
    a substrate;
    a flexible membrane including a central region, wherein the substrate is spatially separated from the flexible membrane by a gap, wherein the central region is configured to contact the substrate in the collapsed state;
    an electrode arrangement comprising a first electrode in contact with the substrate and a second electrode in contact with the flexible membrane; and
    a mass element disposed at the central region of the flexible membrane such that at least a portion of the flexible membrane is disposed between the second electrode and the mass element, wherein the mass element is different from the flexible membrane, the first electrode, and the second electrode, wherein the mass element is configured to force the central region to remain in contact with the substrate while the flexible membrane resonates at a frequency in the collapsed state such that the central region does not temporarily release from the substrate while the flexible membrane resonates at the frequency in the collapsed state; and
  providing the respective electrode arrangement of at least some of the CMUT cells with a voltage including:
    a bias voltage component driving the at least some of the CMUT cells into the collapsed state; and
    a stimulus component for resonating the respective flexible membrane of the at least some CMUT cells at the frequency in said collapsed state, wherein the stimulus component comprises the frequency, wherein the mass element of each of at least some CMUT cells permits release of said central region from the substrate upon reduction or removal of said bias voltage component.

12. The method of claim 11, wherein each electrode arrangement further comprises a third electrode carried by the substrate, wherein the third electrode is located in between the first electrode and the second electrode and is electrically insulated from the first electrode by a dielectric layer, the method further comprising applying the stimulus component across the respective first and second electrodes and applying the bias voltage component to the respective third electrode of the at least some CMUT cells.

13. The method of claim 11, further comprising periodically altering the frequency of the stimulus component to periodically alter a resonance frequency of the at least some CMUT cells.

14. The method of claim 11, further comprising periodically altering the bias voltage component driving the at least some of the CMUT cells into the collapsed state to alter the respective area of the central region of the at least some CMUT cells.

15. The method of claim 11, further comprising providing, in a reception mode, the respective electrode arrangement of at least some of the CMUT cells with a further voltage forcing the at least some CMUT cells in the collapsed state.

16. The ultrasound system of claim 1, wherein the mass element is positioned between the portion of the flexible membrane and an additional portion of the flexible membrane.

* * * * *